United States Patent
Kim et al.

(10) Patent No.: US 12,171,972 B2
(45) Date of Patent: Dec. 24, 2024

(54) GUIDER FOR SEPARATING TUBE

(71) Applicant: Samsung Life Public Welfare Foundation, Seoul (KR)

(72) Inventors: Seung Hyuk Kim, Seoul (KR); Kwang Hyuk Choi, Seoul (KR); Byung Jun Hwang, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 1066 days.

(21) Appl. No.: 16/335,957

(22) PCT Filed: Aug. 24, 2017

(86) PCT No.: PCT/KR2017/009243
§ 371 (c)(1),
(2) Date: Mar. 22, 2019

(87) PCT Pub. No.: WO2018/056592
PCT Pub. Date: Mar. 29, 2018

(65) Prior Publication Data
US 2020/0016392 A1    Jan. 16, 2020

(30) Foreign Application Priority Data
Sep. 23, 2016  (KR) .......................... 10-2016-0122213

(51) Int. Cl.
*A61M 39/10* (2006.01)
*B25B 27/14* (2006.01)

(52) U.S. Cl.
CPC .............. *A61M 39/10* (2013.01); *B25B 27/14* (2013.01); *A61M 2039/1016* (2013.01); *A61M 2209/04* (2013.01)

(58) Field of Classification Search
CPC ........ A61M 25/0637; A61M 2039/087; A61M 2205/58; A61M 2205/586;
(Continued)

(56) References Cited

U.S. PATENT DOCUMENTS

| 298,114  | A | * | 5/1884 | Owen | ................... | E05B 65/006 |
| | | | | | | 269/232 |
| 579,552  | A | * | 3/1897 | Austin | ................... | F16G 11/06 |
| | | | | | | 24/135 R |

(Continued)

FOREIGN PATENT DOCUMENTS

| JP | 2002159579 | 6/2002 |
| JP | 2003154012 | 5/2003 |

(Continued)

OTHER PUBLICATIONS

International Search Report with English Language translation of the International Searching Authority corresponding to International Patent Application No. PCT/KR2017/009243, mailed Dec. 4, 2017. (5 pages).

*Primary Examiner* — Kami A Bosworth
(74) *Attorney, Agent, or Firm* — Myers Bigel, P.A.

(57) ABSTRACT

The present invention relates to a guider for separating a tube, and more particularly, to a guider for easily separating a tube and a catheter which are coupled to each other. The guider for separating a tube according to an exemplary embodiment of the present invention may include: a cylindrical body portion which includes a through space which is opened at both ends thereof and formed to enable a tube to penetrate therethrough; and a wing portion which is connected to an outer surface of the body portion and transmits rotational force to the body portion.

5 Claims, 5 Drawing Sheets

(58) Field of Classification Search
CPC .......... A61M 2209/04; A61M 2209/08; A61M 2209/088; A61M 25/02; A61M 2025/024; A61M 2025/028; A61M 2025/0286; A61M 39/10; A61M 39/165; A61M 2039/1011; A61M 2039/1016; A61M 2039/1066; A61M 2005/3139; F16B 37/0878; B25B 3/00; B25B 5/00; B25B 5/045; B25B 5/067; B25B 5/082; B25B 5/101; B25B 5/125

USPC .................................................. 411/409, 437

See application file for complete search history.

(56) References Cited

U.S. PATENT DOCUMENTS

| | | | | |
|---|---|---|---|---|
| 1,155,012 | A * | 9/1915 | Slee | A61M 2005/3139 604/227 |
| 1,453,418 | A * | 5/1923 | Tessmer | A61M 5/34 604/222 |
| 2,172,461 | A * | 9/1939 | Whitescarver | E04G 17/0658 269/49 |
| 3,388,941 | A * | 6/1968 | Marcus | A61M 5/315 222/467 |
| 3,589,361 | A * | 6/1971 | Loper | A61M 25/0631 604/177 |
| 3,713,442 | A * | 1/1973 | Walter | A61M 25/0637 604/161 |
| 3,834,380 | A * | 9/1974 | Boyd | A61M 25/02 128/DIG. 26 |
| 4,224,937 | A * | 9/1980 | Gordon | A61M 25/02 128/DIG. 26 |
| 4,484,913 | A * | 11/1984 | Swauger | A61M 5/00 604/179 |
| 4,906,233 | A * | 3/1990 | Moriuchi | A61M 25/02 604/174 |
| 4,909,788 | A * | 3/1990 | Egolf | A61M 5/3135 604/227 |
| 5,067,750 | A * | 11/1991 | Minneman | F16B 37/16 285/38 |
| 5,112,312 | A * | 5/1992 | Luther | A61M 25/0637 604/177 |
| 5,169,391 | A * | 12/1992 | Vogel | A61M 25/0637 604/177 |
| 5,498,241 | A * | 3/1996 | Fabozzi | A61M 25/0631 604/177 |
| 5,607,399 | A * | 3/1997 | Grimard | A61M 5/315 604/220 |
| 5,693,032 | A * | 12/1997 | Bierman | A61M 25/02 604/174 |
| 5,817,116 | A | 10/1998 | Takahashi et al. | |
| 6,572,588 | B1 * | 6/2003 | Bierman | A61M 25/02 604/174 |
| 2003/0078540 | A1 * | 4/2003 | Saulenas | A61M 25/0637 604/110 |
| 2003/0163095 | A1 * | 8/2003 | Nakashima | A61M 25/0637 604/177 |
| 2003/0163096 | A1 | 8/2003 | Swenson et al. | |
| 2005/0002757 | A1 * | 1/2005 | Shimizu | F16B 37/0878 411/433 |
| 2007/0239118 | A1 * | 10/2007 | Ono | A61M 25/0631 604/177 |
| 2009/0125003 | A1 * | 5/2009 | Hawkins | A61M 25/02 604/537 |
| 2010/0179483 | A1 * | 7/2010 | Wright | A61M 5/158 604/174 |
| 2011/0264050 | A1 * | 10/2011 | Henry | A61M 25/02 604/177 |
| 2014/0163515 | A1 * | 6/2014 | Hyman | A61M 25/02 604/500 |
| 2015/0112249 | A1 | 4/2015 | Park et al. | |
| 2017/0120016 | A1 * | 5/2017 | Burkholz | A61M 25/0606 |
| 2019/0030312 | A1 * | 1/2019 | Davis | A61J 1/2096 |

FOREIGN PATENT DOCUMENTS

| | | |
|---|---|---|
| JP | 2003260133 | 9/2003 |
| KR | 1019970069045 | 11/1997 |
| KR | 101375973 | 3/2014 |
| KR | 101589982 | 1/2016 |

* cited by examiner

GUIDER FOR SEPARATING TUBE

CROSS-REFERENCE TO RELATED APPLICATIONS

This application is a 35 U.S.C. § 371 national stage application of PCT International Application No. PCT/KR2017/009243, filed on Aug. 24, 2017, which itself claims the benefit of Korean Patent Application No. 10-2016-0122213, filed Sep. 23, 2016, the disclosure and content of both of which are incorporated by reference herein in their entireties. The above-referenced PCT International Application was published in the Korean language as International Publication No. WO 2018/056592 A1 on Mar. 29, 2018.

TECHNICAL FIELD

The present invention relates to a guider for separating a tube, and more particularly, to a guider for easily separating a tube and a catheter which are coupled to each other.

BACKGROUND ART

In a medical field, medical image is obtained by using CT, PET, or MRI to inspect functions of the brain or circulatory organs in human bodies. In this case, an external material such as a contrast agent is injected into a patient's body to increase a degree of image contrast.

To inject the contrast agent into the patient, a tube is connected to a catheter connected to a blood vessel, and the contrast agent is injected into the human body through the tube. A Y-type adapter (or connector) may be used as the catheter for injecting the contrast agent.

To take the medical imaging several times, a process of separating the tube from the catheter connected to the patient and connecting the tube to the catheter again is repeated. However, because the contrast agent has significantly high viscosity, there is a problem in that it is physically difficult to perform the process of separating the catheter and the tube.

DISCLOSURE

Technical Problem

In the related art, a user (e.g., a physician, a nurse, a radiographer, etc.) separates a tube and a catheter by applying grasping power to a connecting portion between the tube and the catheter with bare hands or the user separates the tube and the catheter by holding (or fixing), with medical forceps, the connecting portion between the catheter and the tube and then rotating the connecting portion.

To solve the above-mentioned problem, an object of the present invention is to provide a guider for separating a tube which may be used to enable a user to easily separate the catheter and the tube without great effort. That is, an object of the present invention is to provide a dedicated guider for separating a tube from a catheter.

Technical Solution

An exemplary embodiment of the present invention may provide a guider for separating a tube.

The guider for separating a tube according to an exemplary embodiment of the present invention may include: a cylindrical body portion which includes a through space which is opened at both ends thereof and formed to enable a tube to penetrate therethrough; and a wing portion which is connected to an outer surface of the body portion and transmits rotational force to the body portion.

The body portion according to the exemplary embodiment of the present invention may further include an insertion groove into which the tube is inserted, and the insertion groove may be formed to be entirely open from the upper side to the lower side at one side of the body portion.

The body portion according to the exemplary embodiment of the present invention may further include a fixing groove which is fastened to a protrusion that protrudes from a coupling portion of the tube, and the fixing groove may be formed to be partially open at one side of the body portion.

A hole having a predetermined size may be formed in a part of the wing portion according to the exemplary embodiment of the present invention, and the one or more wing portions may be provided.

The wing portion according to the exemplary embodiment of the present invention may protrude from the outer surface of the body portion to have a predetermined length so as to allow a user to hold and rotate the wing portion, and the wing portion may be formed in a thin plate shape which is curved from the upper side to the lower side of the body portion.

The guider for separating a tube according to the exemplary embodiment of the present invention may be manufactured by using at least one of metal and synthetic resin.

Advantageous Effects

By using the guider for separating a tube according to the exemplary embodiment of the present invention, a user may easily separate the tube coupled to the catheter without great effort. Therefore, it is possible to improve efficiency in performing a process of handling the catheter.

In addition, since the guider for separating a tube according to the exemplary embodiment of the present invention includes the through space, the user may place the guider for separating a tube on an upper portion of a writing tool (e.g., a ballpoint pen) and may use the guider as necessary, and as a result, it is possible to provide the user with convenience for use.

BEST MODE

Figure 1:
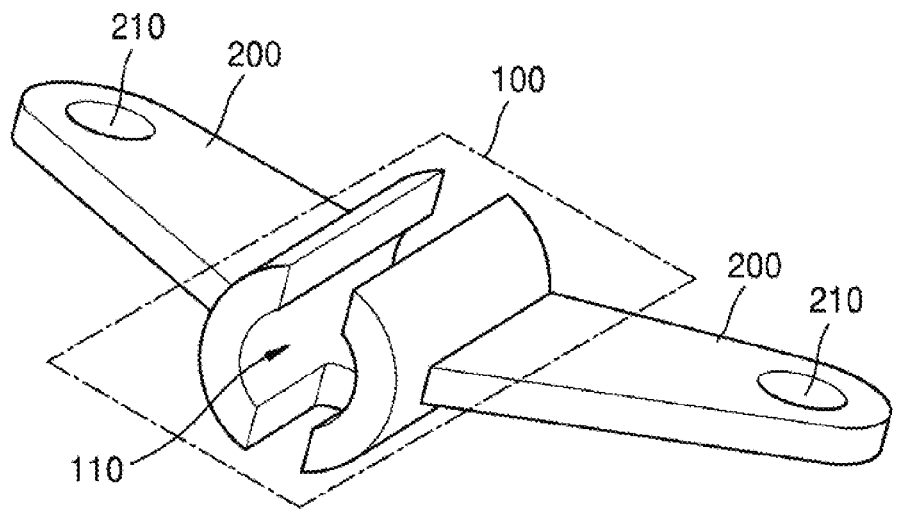
FIG. 1 is a perspective view of a guider for separating a tube according to an exemplary embodiment of the present invention.

An exemplary embodiment of the present invention may provide a guider for separating a tube.

The guider for separating a tube according to the exemplary embodiment of the present invention may include: a cylindrical body portion which includes a through space which is opened at both ends thereof and formed to enable a tube to penetrate therethrough; and a wing portion which is connected to an outer surface of the body portion and transmits rotational force to the body portion.

The body portion according to the exemplary embodiment of the present invention may further include an insertion groove into which the tube is inserted, and the insertion groove may be formed to be entirely open from the upper side to the lower side at one side of the body portion.

The body portion according to the exemplary embodiment of the present invention may further include a fixing groove which is fastened to a protrusion that protrudes from a coupling portion of the tube, and the fixing groove may be formed to be partially open at one side of the body portion.

A hole having a predetermined size may be formed in a part of the wing portion according to the exemplary embodiment of the present invention, and the one or more wing portions may be provided.

The wing portion according to the exemplary embodiment of the present invention may protrude from the outer surface of the body portion to have a predetermined length so as to allow a user to hold and rotate the wing portion, and the wing portion may be formed in a thin plate shape which is curved from the upper side to the lower side of the body portion.

The guider for separating a tube according to the exemplary embodiment of the present invention may be manufactured by using at least one of metal and synthetic resin.

MODE FOR INVENTION

Hereinafter, exemplary embodiments of the present invention will be described in detail with reference to the accompanying drawings so that those with ordinary skill in the art to which the present invention pertains may easily carry out the exemplary embodiments. However, the present invention may be implemented in various different ways, and is not limited to the exemplary embodiments described herein. A part irrelevant to the description will be omitted in the drawings in order to clearly describe the present invention, and similar constituent elements will be designated by similar reference numerals throughout the specification.

The terms used in the present specification will be briefly described, and the present invention will be specifically described.

The terms used in the present invention are selected from general terms currently widely used in the art in consideration of functions in the present invention, but the terms may vary according to the intention of those skilled in the art, precedents, or new technology in the art. Also, specified terms are selected arbitrarily by the applicant, and in this case, the detailed meaning thereof will be described in the detailed description of the invention. Thus, the terms used in the present invention should be defined based on not simple names but the meaning of the terms and the overall description of the present invention.

Throughout the specification, unless explicitly described to the contrary, the word "comprise/include" and variations such as "comprises/includes" or "comprising/including" will be understood to imply the further inclusion of stated elements but not the exclusion of any other elements. In addition, the term "unit", "part", or the like, which is described in the specification, can mean a unit that processes one or more functions or operations. In addition, throughout this specification and the claims, when one constituent element is referred to as being "connected to" another constituent element, one constituent element can be "directly connected to" the other constituent element, and one constituent element can also be "connected to" the other element with other elements therebetween.

Hereinafter, the present invention will be described in detail with reference to the accompanying drawings.

Figure 2A:
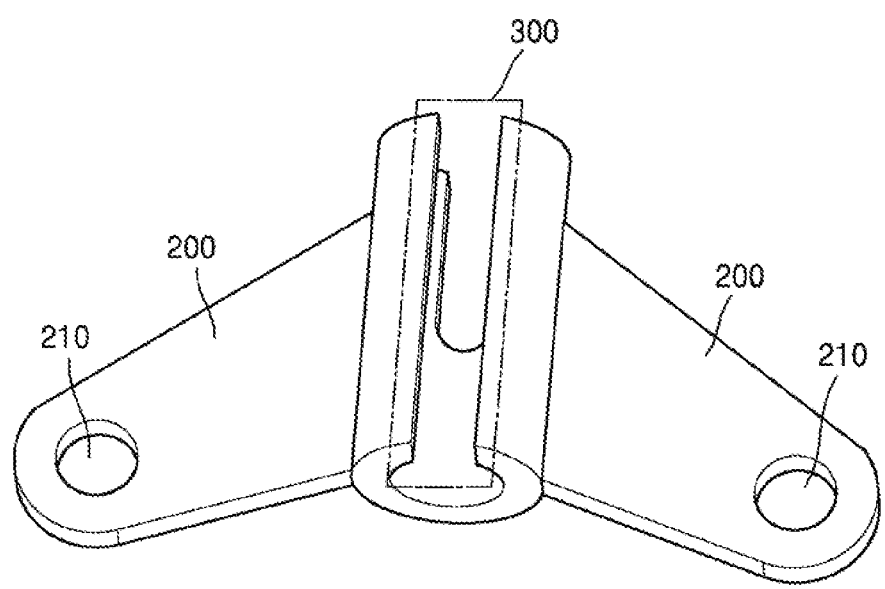
FIG. 2A is a front view of the guider for separating a tube according to the exemplary embodiment of the present invention.
Figure 2B:
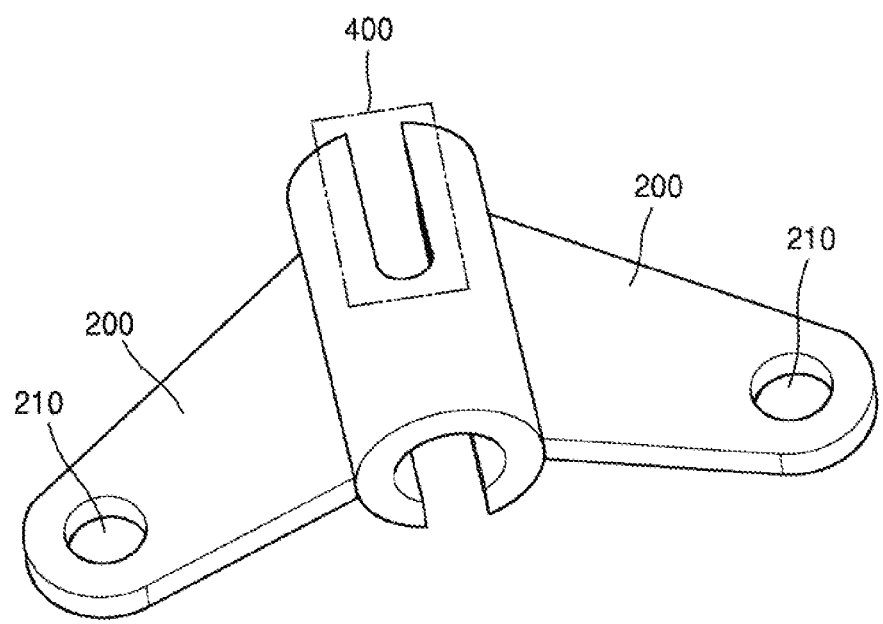
FIG. 2B is a rear view of the guider for separating a tube according to the exemplary embodiment of the present invention.

FIG. 1 is a view illustrating an overall shape of a guider for separating a tube according to an exemplary embodiment of the present invention, FIG. 2A is a front view of the guider for separating a tube according to the exemplary embodiment of the present invention, and FIG. 2B is a rear view of the guider for separating a tube according to the exemplary embodiment of the present invention. In addition, FIG. 3 is a view illustrating a method of fitting a tube with the guider for separating a tube according to the exemplary embodiment of the present invention.

The guider for separating a tube according to the exemplary embodiment of the present invention may include: a cylindrical body portion 100 which includes a through space 110 which is opened at both ends thereof and formed to enable a tube 10 to penetrate therethrough; and a wing portion 200 which is connected to an outer surface of the body portion 100 and transmits rotational force to the body portion 100.

Figure 3:
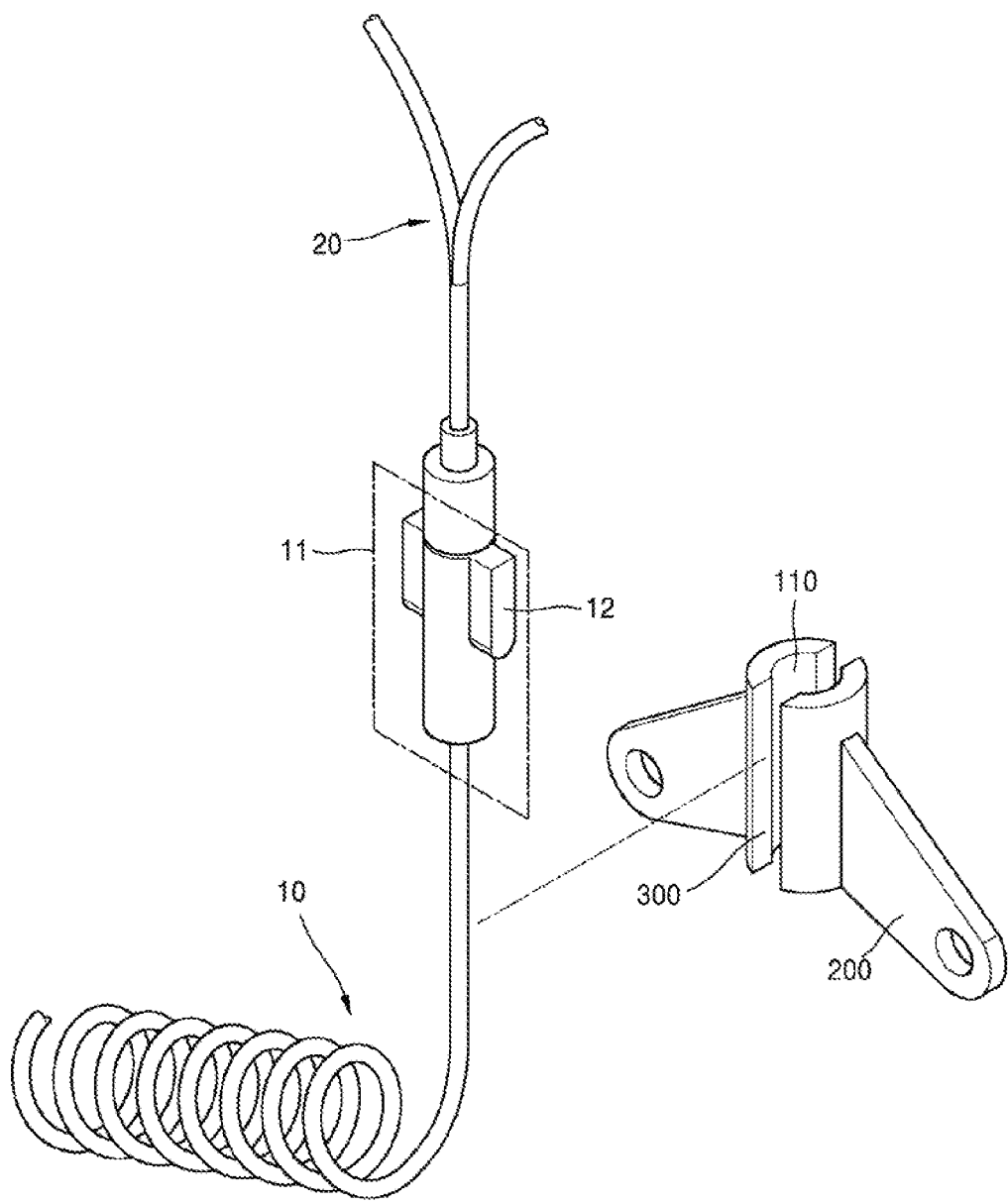
FIG. 3 is a view illustrating a method of fitting a tube with the guider for separating a tube according to the exemplary embodiment of the present invention.

Referring to FIG. 3, a catheter, which is used in the exemplary embodiment of the present invention, may be a Y-type adapter 20, and the tube 10 may be a coil type tube. The Y-type adapter 20 and a tip portion of the tube 10 are formed to have spiral structures, such that the Y-type adapter 20 and the tube 10 may be connected to or separated from each other by rotating the spiral structures.

However, when a contrast agent is injected into the catheter and the tube 10, a significantly large amount of energy is required to rotate and separate, by hand, the Y-type adapter 20 and the tube 10 because of high viscosity of the contrast agent.

According to the exemplary embodiment of the present invention, the guider for separating a tube is fitted with the tube 10 and fixed to a coupling portion 11 of the tube 10, and then the user rotates the wing portions 200 by hand, such that a portion of the tube 10, which is coupled to the Y-type adapter 20, is rotated together with the body portion 100, and as a result, the tube 10 and the Y-type adapter 20 may be easily separated. The coupling portion 11 of the tube 10 according to the exemplary embodiment of the present invention means a tip portion of the tube where the tube 10 and the Y-type adapter 20 are connected to each other.

That is, the wing portions 200 according to the exemplary embodiment of the present invention may increase torque applied to the coupling portion 11 of the tube 10, thereby facilitating the rotation of the coupling portion 11 of the tube 10. That is, the wing portions 200 according to the exemplary embodiment of the present invention may serve to reduce the amount of effort required to rotate the coupling portion 11 of the tube 10.

In addition, each of the wing portions 200 according to the exemplary embodiment of the present invention may be formed in a thin plate shape to increase a contact area with the user's hand. In other words, each of the wing portions 200 may be manufactured to have a predetermined area and a predetermined shape that allow the user to easily hold the wing portions 200. Therefore, the user may hold or rotate the guider for separating a tube by using the wing portions 200.

In other words, when the user rotates the coupling portion 11 of the tube 10 by using the guider for separating a tube according to the exemplary embodiment of the present invention, the effort, which is required to rotate the coupling portion 11 of the tube 10, may be reduced in comparison with the related art, and as a result, it is possible to more easily separate the tube 10 from the Y-type adapter 20 in comparison with the related art.

Therefore, each of the wing portions 200 according to the exemplary embodiment of the present invention may protrude from the outer surface of the body portion 100 so as to have a predetermined length and may be formed in a thin plate shape which is curved from the upper side to the lower side of the body portion 100, so that the user may hold and rotate the wing portions 200.

That is, each of the wing portions 200 according to the exemplary embodiment of the present invention may be shaped such that the user easily holds and rotates the wing portions 200 by hand. In addition, the number of wing portions 200 according to the exemplary embodiment of the present invention may be at least one.

In more detail, only one wing portion 200 may protrude from the body portion 100, or a pair of wing portions 200 may be formed straight, that is, at 180°. In addition, two or more wing portions 200 may be formed at a predetermined angle, for example, at an angle of 120°.

Referring to FIGS. 1 and 2A, the body portion 100 of the guider for separating a tube according to the exemplary embodiment of the present invention may further include an insertion groove 300 into which the tube 10 may be inserted. As illustrated in FIG. 2A, the insertion groove 300 may be formed to be entirely open from the upper side to the lower side at one side of the body portion 100.

The body portion 100 according to the exemplary embodiment of the present invention may further include a fixing groove 400 which is fastened to a protrusion 12 that protrudes from the coupling portion 11 of the tube 10. As illustrated in FIG. 2B, the fixing groove 400 may be formed to be partially open at one side of the body portion 100.

Figure 4:
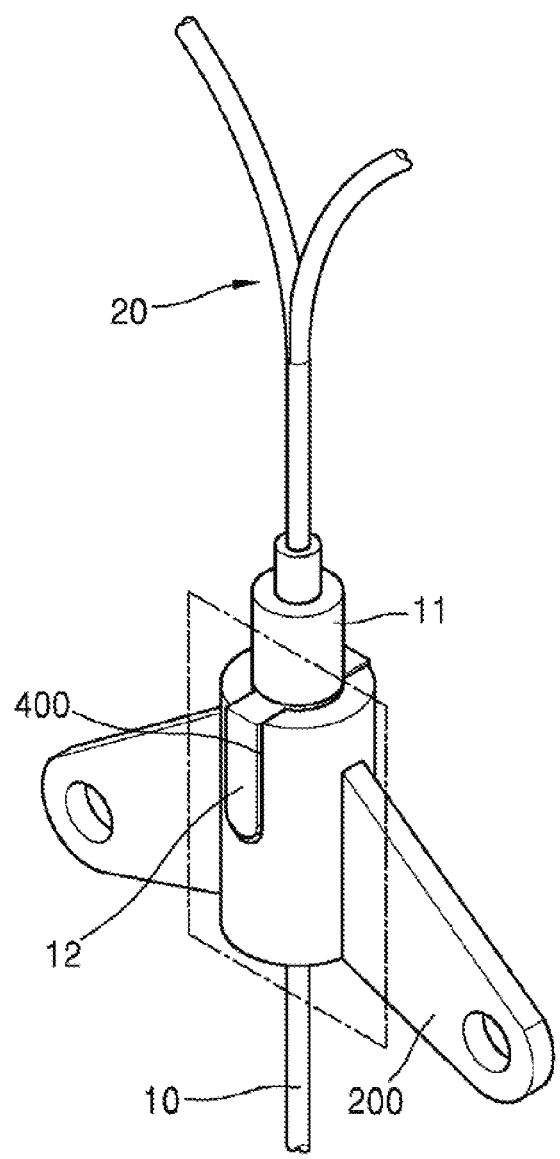
FIG. 4 is a view illustrating a state in which the tube is fastened and fixed to the guider for separating a tube according to the exemplary embodiment of the present invention.

FIG. 4 is a view illustrating a state in which the tube is fastened and fixed to the guider for separating a tube according to the exemplary embodiment of the present invention.

Referring to FIGS. 3 and 4, a thin portion of the tube 10 according to the exemplary embodiment of the present invention may be fitted with the insertion groove 300, and the guider for separating a tube may be moved toward the coupling portion 11 of the tube 10. In this case, the protrusion 12 of the tube 10 may be fitted into the fixing groove 400 according to the exemplary embodiment of the present invention. Therefore, the guider for separating a tube according to the exemplary embodiment of the present invention may be fastened and fixed to the coupling portion 11 of the tube 10.

When separating and rotating the guider for separating a tube with respect to the tube 10 coupled to the Y-type adapter 20, the fixing groove 400 according to the exemplary embodiment of the present invention may prevent the guider for separating a tube from spinning with respect to the tube 10 and allow the guider for separating a tube to rotate together with the coupling portion 11 of the tube 10, such that the tube 10 may be separated from the Y-type adapter 20.

Holes 210 each having a predetermined size may be formed at parts of the wing portions 200 according to the exemplary embodiment of the present invention.

The hole 210 according to the exemplary embodiment of the present invention is held or fitted with a latch including a nail or a pin, and as a result, the guider for separating a tube may be stored at a specific location. That is, the hole 210 according to the exemplary embodiment of the present invention may provide a loss prevention function so that the user does not lose the guider for separating a tube.

The guider for separating a tube according to the exemplary embodiment of the present invention may be manufactured by using at least one of metal and synthetic resin. In other words, the guider for separating a tube according to the exemplary embodiment of the present invention may be manufactured by using a material such as plastic having high strength in addition to iron.

Figure 5:
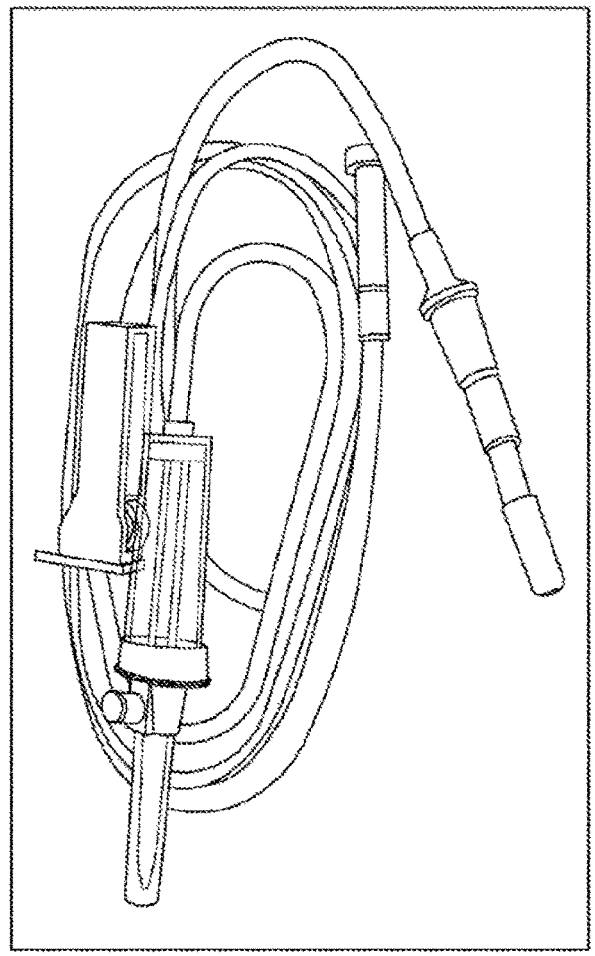
FIG. 5 is a view illustrating an example of a replaceable infusion solution set to which the guider for separating a tube according to the exemplary embodiment of the present invention may be applied.
Figure 5:
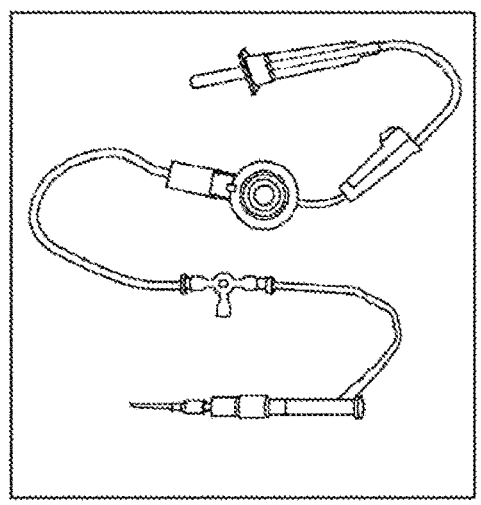

FIG. 5 is a view illustrating an example of a replaceable infusion solution set to which the guider for separating a tube according to the exemplary embodiment of the present invention may be applied.

The description, which has been made with reference to FIGS. 1 to 4, is just for convenience of description, and the guider for separating a tube according to the exemplary embodiment of the present invention may be applied to and used for any infusion solution set that needs to be replaced. In other words, as illustrated in FIG. 5, various infusion solution sets (for example, see FIG. 5A or 5B) are used in medical institutions. The guider for separating a tube according to the exemplary embodiment of the present invention may be used for various infusion solution sets. That is, the guider for separating a tube according to the exemplary embodiment of the present invention may be connected to the connecting portion between the catheter and the tube and rotated so that the user may easily separate the connecting portions between the tube and the catheter.

It will be appreciated that the exemplary embodiments of the present invention have been described above for purposes of illustration, and those skilled in the art may understand that the present invention may be easily modified in other specific forms without changing the technical spirit or the essential features of the present invention. Therefore, it should be understood that the above-described exemplary embodiments are illustrative in all aspects and do not limit the present invention. For example, each component described as a single type may be carried out in a distributed manner. Likewise, components described as a distributed type can be carried out in a combined type.

The scope of the present invention is represented by the claims to be described below rather than the detailed description, and it should be interpreted that the meaning and scope of the claims and all the changes or modified forms derived from the equivalent concepts thereto fall within the scope of the present invention.

The invention claimed is:

1. A guider for separating a tube, the guider comprising:
 a cylindrical body portion which includes a through space including two ends, the through space being opened at the two ends and being formed to enable a tube to penetrate through the body portion; and
 two wing portions connected to an outer surface of the body portion and configured to transmit rotational force to the body portion,
 wherein the body portion further includes a fixing groove which is configured to be fastened to a protrusion that protrudes from a coupling portion of the tube, and
 wherein the fixing groove is formed to be partially open at one side of the body portion,
 wherein the body portion further includes an insertion groove configured to allow a tube to be inserted therein, and the insertion groove is formed to be entirely open from an upper side of the body portion to a lower side of the body portion at one side of the body portion and the fixing groove is diametrically opposite the insertion groove, wherein when the tube is inserted into the insertion groove and the fixing groove is fastened to the protrusion that protrudes from the coupling portion of the tube, the two wing portions are each configured with a curved plate shape that is curved from the upper side of the body portion to the lower side of the body portion and extends away from the body portion continuously at an oblique angle immediately adjacent the body portion such that, when a user rotates the two wing portions, the two wing portions increase a torque applied to the protrusion to thereby rotate the coupling portion of the tube, wherein the two wing portions are diametrically opposed along a plane extending through a middle region of the body portion.

2. The guider of claim 1, wherein a hole having a predetermined size is formed in a part of the two wing portions.

3. The guider of claim 1, wherein the two wing portions protrude from the outer surface of the body portion to have a predetermined length so as to allow a user to hold and rotate the two wing portions.

4. The guider of claim 1, wherein the guider is manufactured by using at least one of metal and synthetic resin.

5. The guider of claim 1, wherein the two wing portions are mounted on opposite sides of the cylindrical body portion, and the fixing groove is between the wing portions along the cylindrical body portion.

* * * * *